(12) United States Patent
Yuasa

(10) Patent No.: US 10,561,060 B2
(45) Date of Patent: Feb. 18, 2020

(54) CROP GROWTH MEASUREMENT DEVICE

(71) Applicant: TOPCON CORPORATION, Itabashi-ku, Tokyo (JP)

(72) Inventor: Taichi Yuasa, Tokyo (JP)

(73) Assignee: TOPCON CORPORATION, Itabashi-ku, Tokyo (JP)

( * ) Notice: Subject to any disclaimer, the term of this patent is extended or adjusted under 35 U.S.C. 154(b) by 0 days.

(21) Appl. No.: 16/106,201

(22) Filed: Aug. 21, 2018

(65) Prior Publication Data

US 2019/0069476 A1 Mar. 7, 2019

(30) Foreign Application Priority Data

Sep. 7, 2017 (JP) .................................. 2017-171922

(51) Int. Cl.
*G01J 3/02* (2006.01)
*A01C 21/00* (2006.01)
*G01J 3/10* (2006.01)
*G01J 3/427* (2006.01)
*G01N 21/3563* (2014.01)
*G01N 21/31* (2006.01)
(Continued)

(52) U.S. Cl.
CPC .......... *A01C 21/007* (2013.01); *G01J 3/0286* (2013.01); *G01J 3/108* (2013.01); *G01J 3/427* (2013.01); *G01N 21/3563* (2013.01); *G01J 2003/4275* (2013.01); *G01N 21/359* (2013.01); *G01N 2021/1797* (2013.01); *G01N 2021/3181* (2013.01); *G01N 2201/0627* (2013.01); *G01N 2201/0691* (2013.01)

(58) Field of Classification Search
CPC ...... A01C 21/007; G01J 3/0208; G01J 3/021; G01J 3/0218; G01J 3/0224; G01J 3/024; G01J 3/0272; G01J 3/10; G01J 3/108
USPC ........................................................ 356/634
See application file for complete search history.

(56) References Cited

U.S. PATENT DOCUMENTS

| 7,910,876 | B2 | 3/2011 | Kumagai et al. |
| 8,822,904 | B2 * | 9/2014 | Hayashi .............. A01M 7/0089 250/205 |
| 9,921,162 | B2 * | 3/2018 | Tischler ............. G01N 21/6486 |

(Continued)

FOREIGN PATENT DOCUMENTS

JP 5522913 B2 6/2014

*Primary Examiner* — Roy M Punnoose
(74) *Attorney, Agent, or Firm* — Chiesa Shahinian & Giantomasi PC

(57) ABSTRACT

A light source section configured to couple a plurality of laser beams having different wavelengths and emit measuring light; an illuminating section configured to illuminate a measurement target at a predetermined angle; a light receiving section configured to receive reflected measuring light from the measurement target; and a controlling section configured to compute a reflectance at each of the wavelengths, based on a light receiving result. The light source section includes: a first and a second light source configured to emit each laser beams having different wavelengths; and a dichroic mirror disposed in optical axes of the laser beams intersected, configured to combine the laser beams. The light receiving section includes: a first, a second and a third light receiving unit configured to receive the reflected measuring light from different distance. The controlling section is configured to select which of results from each light receiving unit to use.

18 Claims, 21 Drawing Sheets

(51) Int. Cl.
  *G01N 21/359* (2014.01)
  *G01N 21/17* (2006.01)

(56) References Cited

U.S. PATENT DOCUMENTS

2005/0098713 A1* 5/2005 Holland .................... G01J 3/10
  250/221
2011/0186752 A1* 8/2011 Moise .................... G01J 3/4406
  250/459.1

* cited by examiner

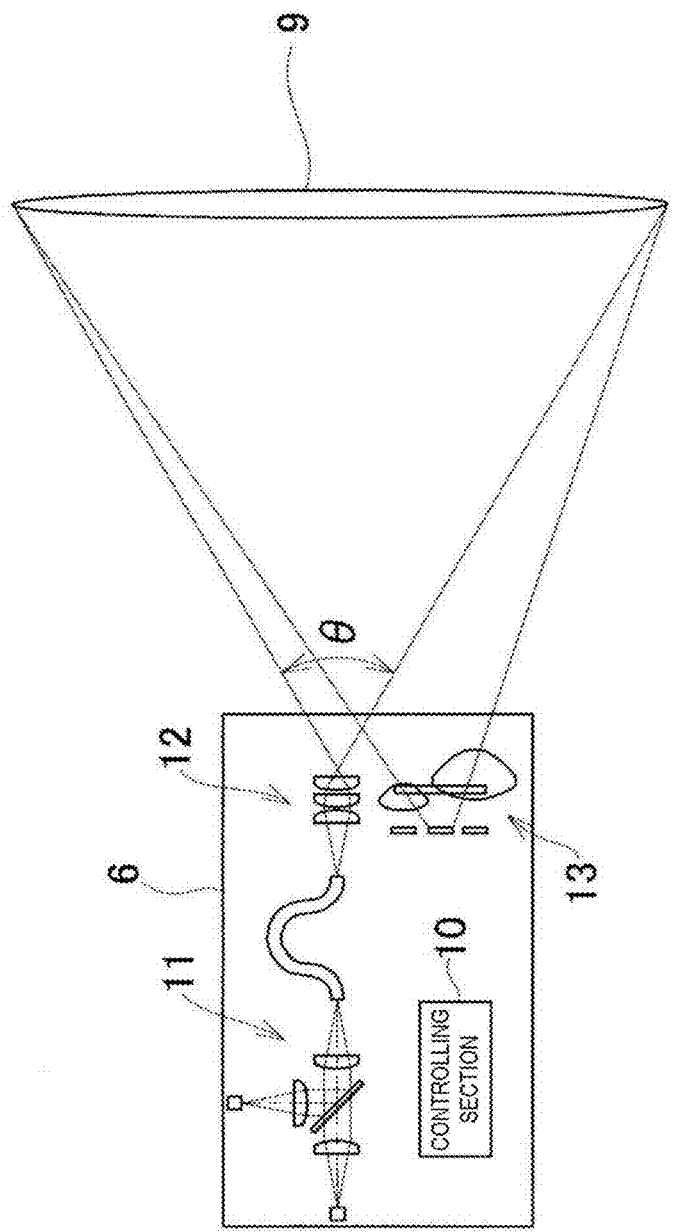

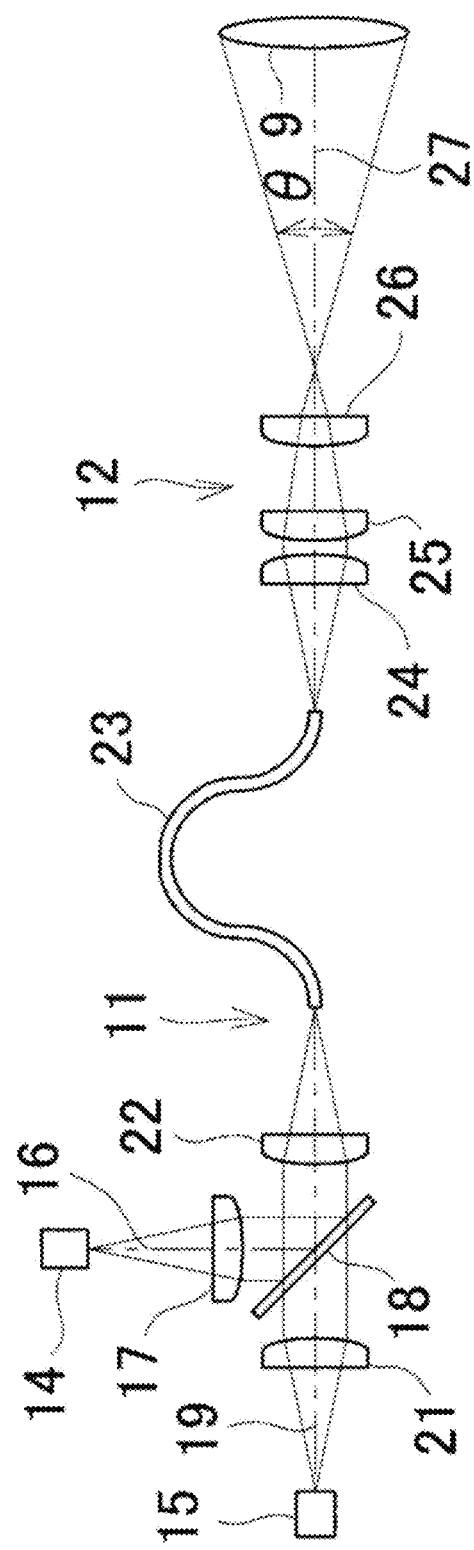

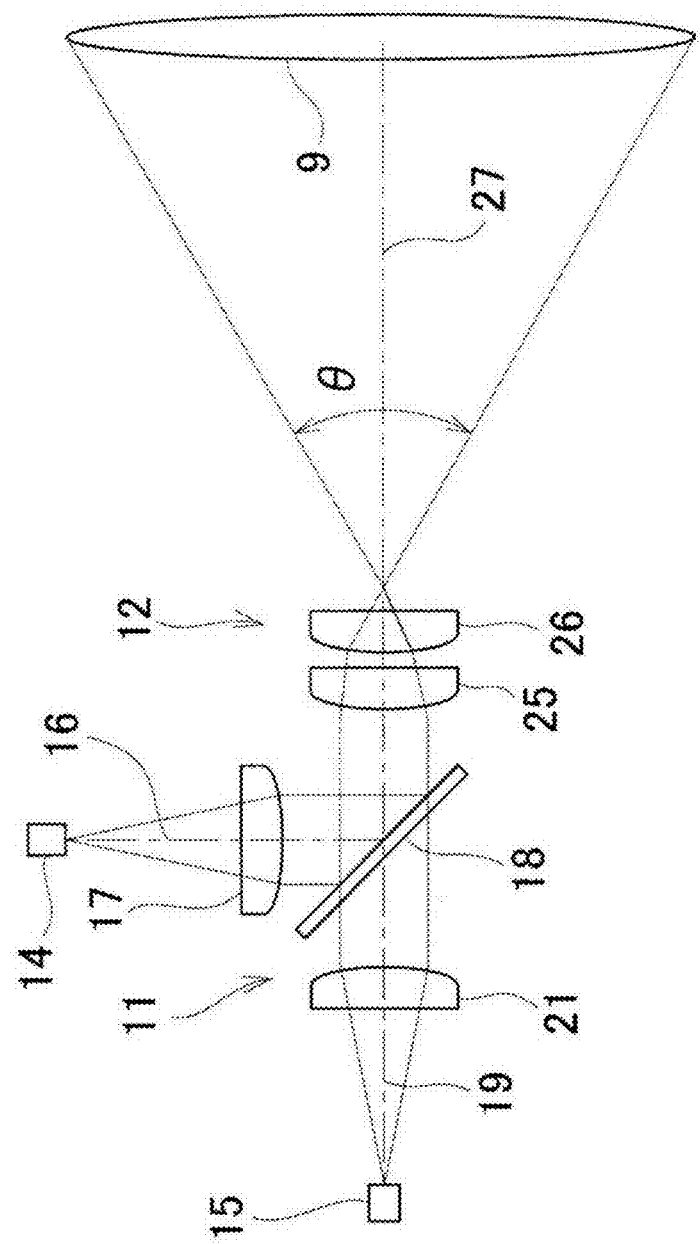

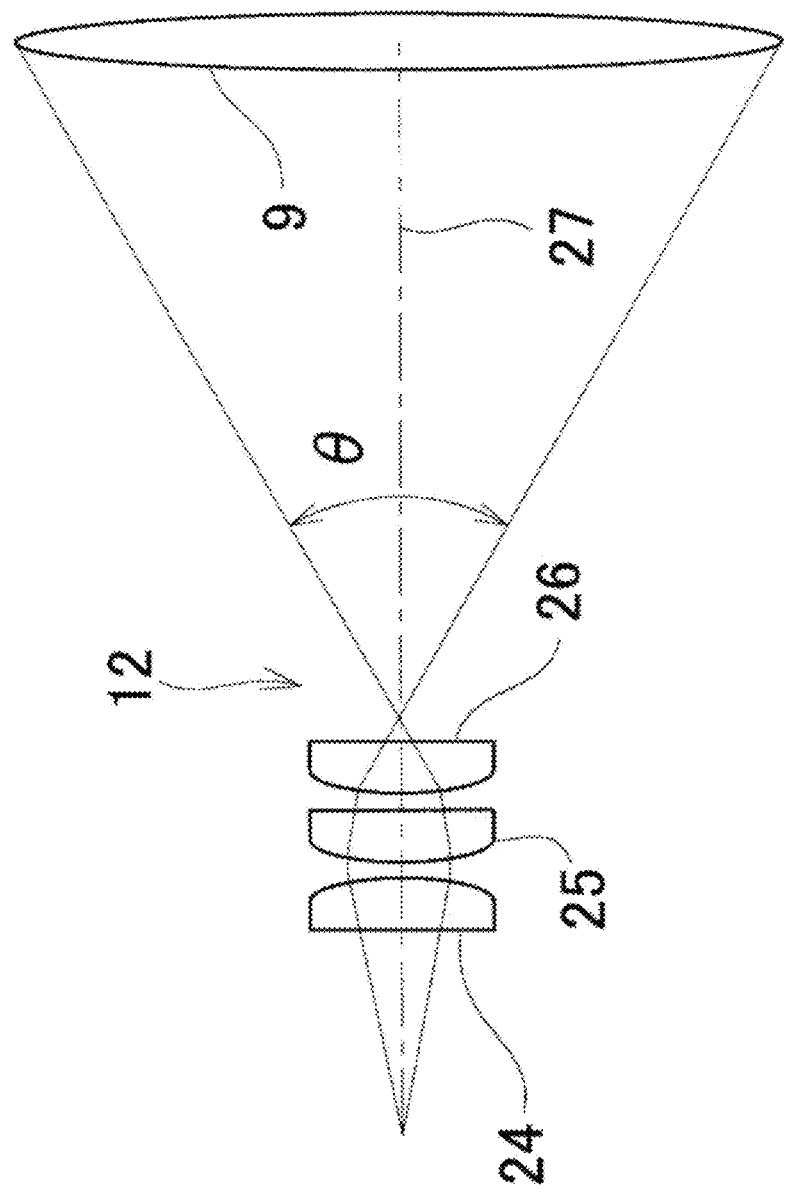

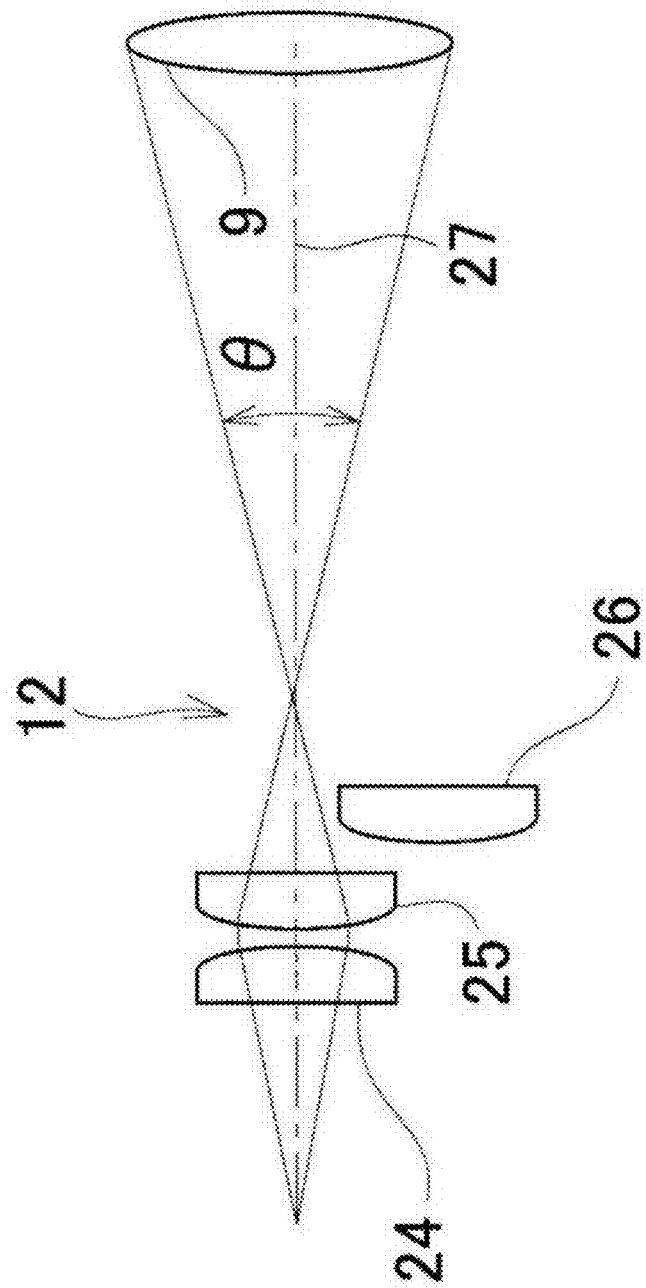

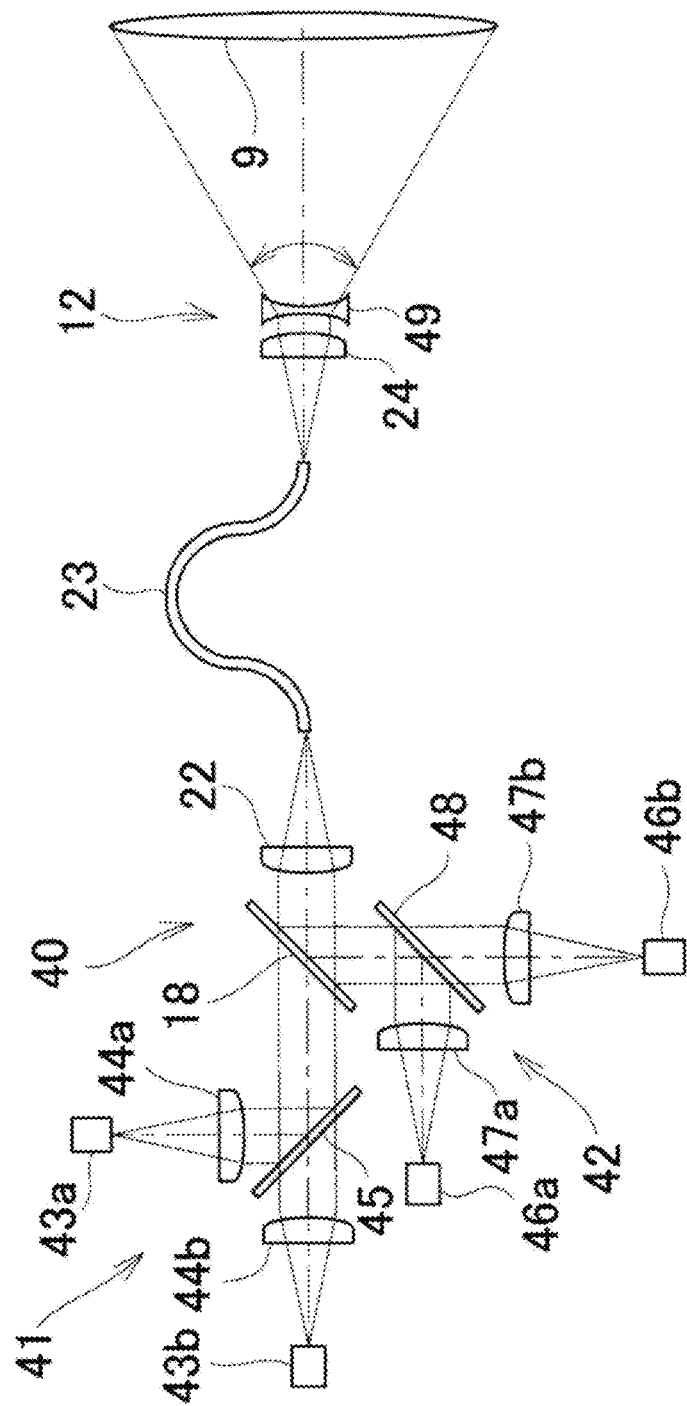

CROP GROWTH MEASUREMENT DEVICE

CROSS-REFERENCE TO RELATED APPLICATION

This application is based upon and claims benefit of priority from Japanese Patent Application No. 2017-171922, filed Sep. 7, 2017, the entire contents of which are incorporated herein by reference.

TECHNICAL FIELD

The present invention relates to a measurement device configured to illuminate crops with measuring light and analyze reflected light to measure the growth state of the crops.

BACKGROUND

In the related art, to know the growth state of crops, such as rice, wheat, and soybeans, for fertilization control, water volume control, and the like, a light source, such as a laser diode, illuminates the crops with measuring light, and reflected light is calculated and analyzed to measure the nitrogen content in the crops and the like. This measurement is performed by a measurement device mounted in a movable body, such as a tractor and a small Unmanned Aerial Vehicle (UAV), a hand-held measurement device carried by an operative, or the like.

A measurement device in the related art has a narrow measurable range and can perform measurement at a limited distance only, so that a single measurement device cannot perform measurement freely at short to long distances.

Thus, a measurement device having an appropriate measurable range is required depending on the distance (altitude) to crops to be measured. This indicates that multiple measurement devices are required, resulting in an increase in cost and complex work.

SUMMARY OF THE EMBODIMENTS

An object of the invention is to provide a measurement device capable of measuring the growth state of crops at short to long distances.

According to an aspect of the invention, a measurement device includes: a light source section configured to couple a plurality of laser beams having different wavelengths and to emit measuring light; an illuminating section configured to illuminate a measurement target with the measuring light at a predetermined illuminating angle; a light receiving section configured to receive reflected measuring light from the measurement target; and a controlling section configured to compute a reflectance at each of the wavelengths, based on a light receiving result. The light source section includes: a first light source configured to emit a laser beam having a first wavelength; a second light source configured to emit a laser beam having a second wavelength different from a wavelength of the first light source; and a dichroic mirror disposed in a position in which optical axes of the laser beams having the two wavelengths intersect, the dichroic mirror being configured to transmit one of the laser beams and reflect the other of the laser beams and to combine the laser beams having the two wavelengths. The light receiving section includes: a first light receiving unit configured to receive the reflected measuring light from a short distance; a second light receiving unit configured to receive the reflected measuring light from a medium distance; and a third light receiving unit configured to receive the reflected measuring light from a long distance. The controlling section is configured to select which of light receiving results from the first light receiving unit, the second receiving unit, and the third receiving unit to use, based on a distance to the measurement target.

According to an aspect of the invention, in the measurement device, the first light receiving unit includes: a first light receiving lens including a row of cylindrical lenses having generatrix directions coinciding with a major axis direction of the reflected measuring light; and a first light receiving element configured to receive the reflected measuring light condensed through the first light receiving lens, the second light receiving unit includes: at least one second light receiving lens having a rotationally symmetric shape and a large numerical aperture; and at least one second light receiving element configured to receive the reflected measuring light condensed through the at least one second light receiving lens, the third light receiving unit includes: a third light receiving lens having a larger diameter and a longer focal length than a diameter and a focal length of the at least one second light receiving lens and having a rotationally symmetric shape and a large numerical aperture; and a third light receiving element configured to receive the reflected measuring light condensed through the third light receiving lens, and the controlling section is configured to use a light receiving result from the first light receiving element in measurement at a short distance, to use light receiving results from the first light receiving element and the at least one second light receiving element in measurement at a medium distance, and to use light receiving results from the first light receiving element, the at least one second light receiving element, and the third light receiving element in measurement at a long distance.

According to an aspect of the invention, in the measurement device, the illuminating section includes an illuminating angle varying unit disposed on an optical axis of the measuring light, and the controlling section is configured to vary an illuminating angle of the measuring light, based on a distance to the measurement target.

According to an aspect of the invention, in the measurement device, the illuminating angle varying unit includes: a first cylindrical lens provided in a fixed manner; and a second cylindrical lens provided movably along the optical axis of the measuring light, and the illuminating angle varying unit allows the illuminating angle to be varied in accordance with a varied distance between the first cylindrical lens and the second cylindrical lens.

According to an aspect of the invention, in the measurement device, the illuminating angle varying unit includes: a first cylindrical lens provided in a fixed manner; and a second cylindrical lens removably provided on the optical axis of the measuring light.

According to an aspect of the invention, in the measurement device, the light source section further includes an optical fiber through which the measuring light combined by the dichroic mirror and having the two wavelengths is guided to uniformize light intensity.

According to an aspect of the invention, in the measurement device, the first light source includes: two light emitting elements configured to emit laser beams having a first wavelength and arranged with polarization directions different from each other; and a first deflecting mirror configured to combine the laser beams emitted from the two light emitting elements, and the second light source includes: two light emitting elements configured to emit laser beams having a second wavelength and arranged with polarization directions different from each other; and a second deflecting mirror configured to combine the laser beams emitted from the two light emitting elements.

According to an aspect of the invention, the measurement device further includes: a plurality of light source sections; and a fiber combiner configured to combine a plurality of rays of the measuring light emitted from the plurality of light source sections.

According to an aspect of the invention, in the measurement device, the light receiving section includes a light receiving element arranged with a diagonal line coinciding or substantially coinciding with a major axis of the reflected measuring light.

According to an aspect of the invention, the measurement device includes: a light source section configured to couple a plurality of laser beams having different wavelengths and to emit measuring light; an illuminating section configured to illuminate a measurement target with the measuring light at a predetermined illuminating angle; a light receiving section configured to receive reflected measuring light from the measurement target; and a controlling section configured to compute a reflectance at each of the wavelengths on a basis of a light receiving result. The light source section includes: a first light source configured to emit a laser beam having a first wavelength; a second light source configured to emit a laser beam having a second wavelength different from that of the first light source; and a dichroic mirror disposed in a position in which optical axes of the laser beams having the two wavelengths intersect, the dichroic mirror being configured to transmit one of the laser beams and reflect the other of the laser beams and to combine the laser beams having the two wavelengths. The light receiving section includes: a first light receiving unit configured to receive the reflected measuring light from a short distance; a second light receiving unit configured to receive the reflected measuring light from a medium distance; and a third light receiving unit configured to receive the reflected measuring light from a long distance. The controlling section is configured to select which of light receiving results from the first light receiving unit, the second light receiving unit, and the third light receiving unit to use, based on a distance to the measurement target. This configuration enables a single measurement device to perform measurement at short to long distances and thus exhibits excellent effect of reducing measurement cost.

BRIEF DESCRIPTION OF THE DRAWINGS

FIGS. 2A and 2B are schematic configuration diagrams of a measurement device according to the first embodiment of the invention.

FIGS. 3A to 3C are schematic configuration diagrams of a coupling section and an illuminating section of a measurement device, and FIG. 3A illustrates the case of measurement at a short distance, FIG. 3B illustrates the case of measurement at a medium distance, and FIG. 3C illustrates the case of measurement at a long distance.

FIG. 7 is a schematic configuration diagram of a modification of a measurement device according to the first embodiment of the invention.

FIGS. 9A and 9B are schematic configuration diagrams of a modification of a measurement device according to the first embodiment of the invention.

FIG. 11 is a schematic configuration diagram of a measurement device according to a second embodiment of the invention.

DESCRIPTION OF EMBODIMENTS

Embodiments of the invention will be described next with reference to the drawings.

Figure 1:
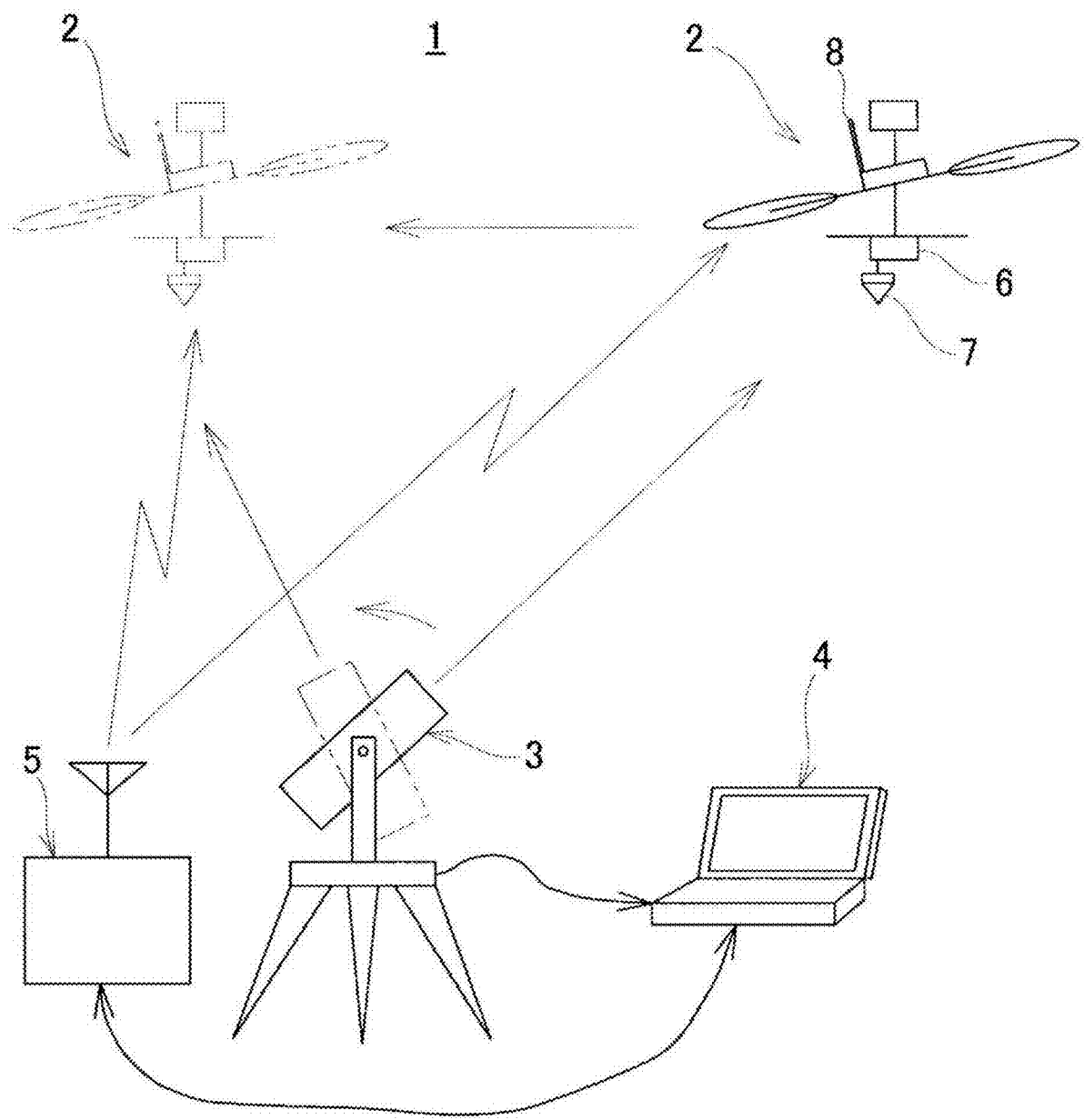
FIG. 1 is a schematic diagram of a measurement system including a measurement device according to a first embodiment of the invention.

FIG. 1 schematically illustrates a measurement system 1 in which a measurement device according to a first embodiment of the invention is mounted in a UAV.

In FIG. 1, 2 denotes the UAV, and 3 denotes a surveying device having a tracking function, for example, a total station. In FIG. 1, 4 denotes a remote operation device (for example, a computing device, such as a PC, a smartphone, and a tablet), and 5 denotes a communication device. The communication device 5 is connected with the remote operation device 4 in a prescribed manner, for example, by wire or wirelessly, can exchange data with the remote operation device 4, and performs data communication with the UAV 2 and the total station 3.

Flight of the UAV 2 is controlled through remote operation with the remote operation device 4, or the UAV 2 autonomously flies on the basis of a flight program.

The UAV 2 includes a measurement device 6, a prism 7, and a communication device 8 mounted therein. The measurement device 6 is supported with the optical axis of the measurement device 6 always extending vertically or substantially vertically, and is integrated with the prism 7 while having a known positional relationship with the prism 7.

Note that the measurement device 6 may be provided with an inclination sensor configured to detect inclination of the measurement device 6. In a case where inclination of the optical axis of the measurement device 6 is acquired on the basis of a detection result from the inclination sensor and a measurement result from the measurement device 6 is corrected on the basis of the inclination of the optical axis, the measurement device 6 is not required to be supported with its optical axis extending vertically or substantially vertically.

The measurement device 6 illuminates a measurement target object surface (for example, an agricultural field) with measuring light 9 having a plurality of wavelengths (see FIGS. 2A and 2B), detects the amount of light received from measurement targets (for example, crops) at each of the wavelength, and measures a reflectance at each of the wavelengths from the amount of light received. The measured reflectance is sent through the communication device 8 and the communication device 5 to the remote operation device 4, as a measurement result from the measurement device 6.

The total station 3 is installed in a known point (a point of which the three-dimensional coordinates are known), is collimated to the prism 7, and measures the position (three-dimensional coordinates) of the prism 7 while tracking the prism 7. The positional data on the prism 7 acquired through the measurement by the total station 3 is sent through the communication device 5 to the remote operation device 4. Note that the UAV 2 may be provided with a GNSS device that measures the position of the UAV 2 (i.e., the position of the measurement device 6).

The remote operation device 4 correlates the measured position with the measurement result on the basis of the timing at which the total station 3 measures the position of the prism 7 and the timing of the measurement by the measurement device 6. This enables measurement of a reflectance at each of the wavelengths at a desired position in the agricultural field and measurement of the growth state of the crops on the basis of the reflectance.

Measurement of the growth state of the crops based on the reflectance indicates measurement of the amount of chlorophyll contained in leaves of the crops based on the reflectance at a specific wavelength, for example. By measuring the amount of chlorophyll, the nutritional state of the crops can be accurately known, and appropriate fertilization control can be performed.

Note that the actual measured position in measurement of the growth state is not a prism reference position (i.e., the optical center of the prism 7) but a reference position of the measurement device 6. Thus, when the measured position is correlated with the measurement result, a difference between the prism reference position and the measurement reference position is required to be taken into consideration in computation.

In the present embodiment, the prism 7 is directly attached to the measurement device 6. The measurement device 6 and the prism 7 are thus integrated, and the positional relationship between the prism reference position and the measurement reference position is fixed.

The measurement device 6 according to the first embodiment of the invention will be described next with reference to FIGS. 2A, 2B to 5A, 5B.

The measurement device 6 mainly includes a light source section 11, an illuminating section 12, a light receiving section 13, and a controlling section 10.

The light source section 11 includes a plurality of light sources and has a coupling function configured to combine a plurality of light beams having different wavelengths and emitted from the light sources. The present embodiment includes a first light emitting element 14 (for example, a laser diode) configured to emit a first laser beam having a wavelength of 735 nm and a second light emitting element 15 (for example, a laser diode) configured to emit a second laser beam having a wavelength of 808 nm. Note that the first light emitting element 14 and the second light emitting element 15 may be composed of an LED or a multiwavelength light source, and a light beam having a specific wavelength may be filtered with a wavelength selection filter.

A first collimator lens 17 and a dichroic mirror 18 are disposed on a first optical axis 16 of the first laser beam. A second collimator lens 21, the dichroic mirror 18, a condenser lens 22, and an incident end of an optical fiber 23 are disposed on a second optical axis 19 of the second laser beam. Note that a mirror having a curved surface or a free-form surface may be used instead of the first collimator lens 17, the second collimator lens 21, and the condenser lens 22.

The dichroic mirror 18 has such optical properties as to reflect the first laser beam and transmit the second laser beam. The first laser beam is reflected off the dichroic mirror 18 and is combined with the second laser beam.

The first laser beam emitted from the first light emitting element 14 is converted into a parallel beam by the first collimator lens 17 and is reflected off the dichroic mirror 18. The second laser beam emitted from the second light emitting element 15 is converted into a parallel beam by the second collimator lens 21 and passes through the dichroic mirror 18.

The first laser beam and the second laser beam are combined, through the dichroic mirror 18, into the measuring light 9 having two wavelengths. The measuring light 9 is condensed onto the condenser lens 22 and is incident on the incident end of the optical fiber 23. The measuring light 9 is mixed so that the spatial distribution and angular distribution of the light intensity are uniformized while being guided through the optical fiber 23, and is emitted from an emitting end of the optical fiber 23 toward the illuminating section 12.

The illuminating section 12 includes a third collimator lens 24, a first cylindrical lens 25 having a convex surface, and a second cylindrical lens 26 having a convex surface. The third collimator lens 24, the first cylindrical lens 25, and the second cylindrical lens 26 are disposed on an illumination optical axis 27 of the measuring light 9 emitted from the emitting end of the optical fiber 23. Note that a mirror having a curved surface or a free-form surface may be used instead of the third collimator lens 24.

The second cylindrical lens 26 can move along the illumination optical axis 27 with, for example, a motor (not illustrated), so that the distance between the first cylindrical lens 25 and the second cylindrical lens 26 is adjustable. Note that the first cylindrical lens 25 and the second cylindrical lens 26 constitute an illuminating angle varying unit.

The measuring light 9 emitted from the emitting end of the optical fiber 23 is converted into a parallel beam by the third collimator lens 24. Then, the measuring light 9 is condensed and diffused in the vertical direction in FIGS. 2A and 2B on paper (the major axis direction) by the first cylindrical lens 25 and the second cylindrical lens 26, and illuminates a measurement target object. Since the measuring light 9 is uniformized while being guided through the optical fiber 23, the measuring light 9 emitted from the illuminating section 12 has a small difference in the light intensity distribution based on a difference in wavelength between the first light emitting element 14 and the second light emitting element 15.

Figure 2B:
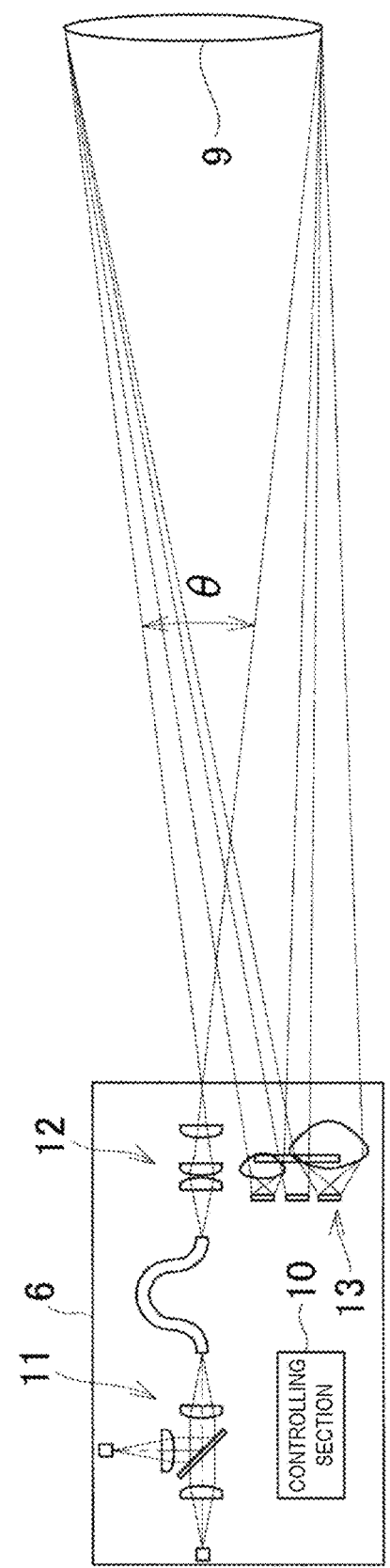
Figure 3A:
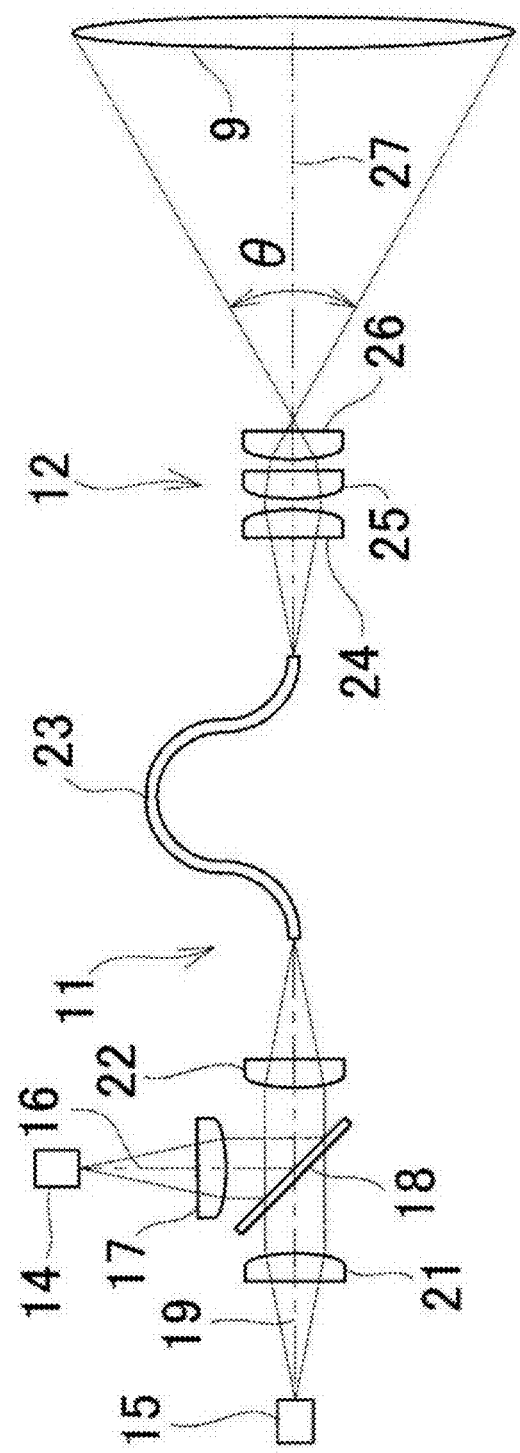

At this time, the angle formed by the diffused measuring light 9 (illuminating angle in the major axis direction of the beam) $\theta$ varies in the range from, for example, 10° to 70° depending on the distance between the first cylindrical lens 25 and the second cylindrical lens 26. As illustrated in FIGS. 2A and 3A, as the distance between the first cylindrical lens 25 and the second cylindrical lens 26 is shorter, the illuminating angle $\theta$ of the measuring light 9 increases. As illustrated in FIGS. 2B and 3C, as the distance between the first cylindrical lens 25 and the second cylindrical lens 26 is longer, the illuminating angle θ of the measuring light 9 decreases.

Note that the illuminating angle of the measuring light 9 in the minor axis direction (direction perpendicular to the paper in FIGS. 2A and 2B) is approximately from 1° to 5° and is determined by the core diameter of the optical fiber 23 and the focal length of the third collimator lens 24 because the first cylindrical lens 25 and the second cylindrical lens 26 have no optical action (refractive power) in the minor axis direction. Thus, even in a case where the distance between the first cylindrical lens 25 and the second cylindrical lens 26 is varied, the illuminating angle of the measuring light 9 in the minor axis direction remains the same. Consequently, by moving the second cylindrical lens 26 along the illumination optical axis 27, the illuminating angle of the measuring light 9 can be varied only in the major axis direction.

Since the illuminating angle of the measuring light 9 can be varied in the major axis direction, the illuminating angle θ of the measuring light 9 can be freely adjusted to be an angle (from approximately 40° to approximately 70°) appropriate for a short distance (from approximately 5 m to approximately 10 m), an angle (from approximately 20° to approximately 40°) appropriate for a medium distance (from approximately 10 m to approximately 20 m), or an angle (from approximately 10° to approximately 20°) appropriate for a long distance (from approximately 20 m to approximately 30 m).

Figure 4A:
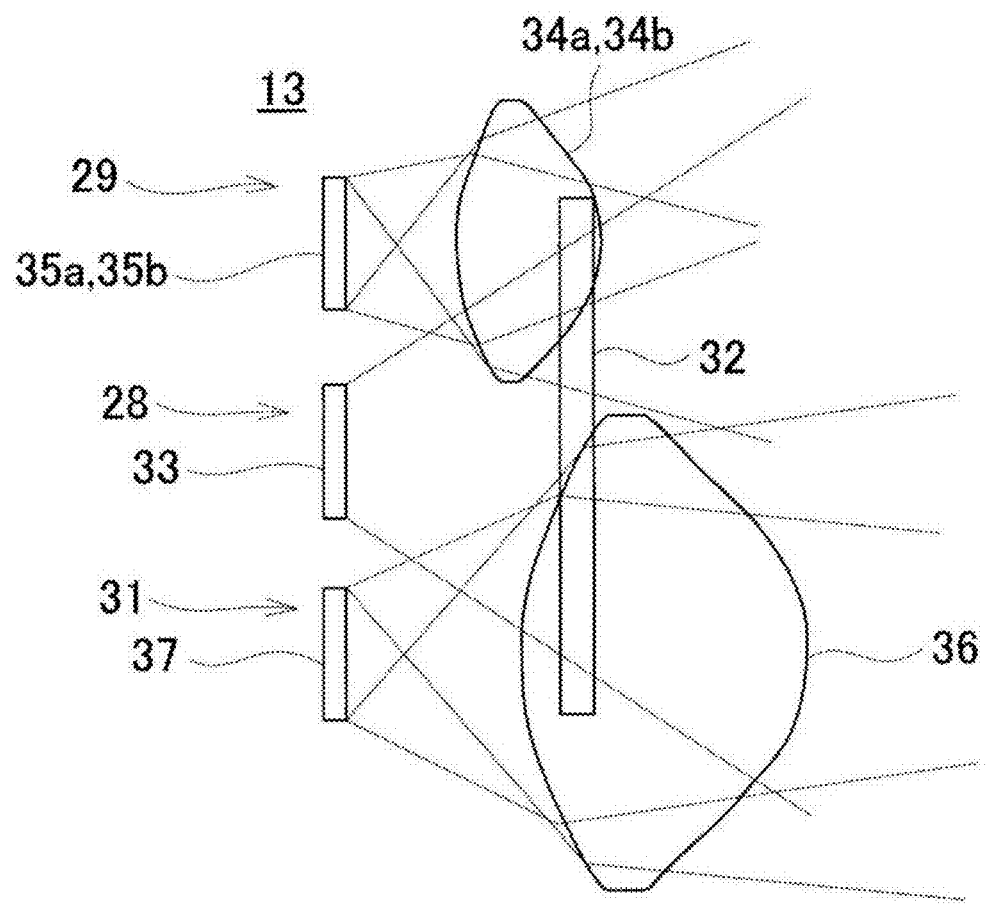
FIG. 4A is a schematic side view of a light receiving section of a measurement device.
Figure 4B:
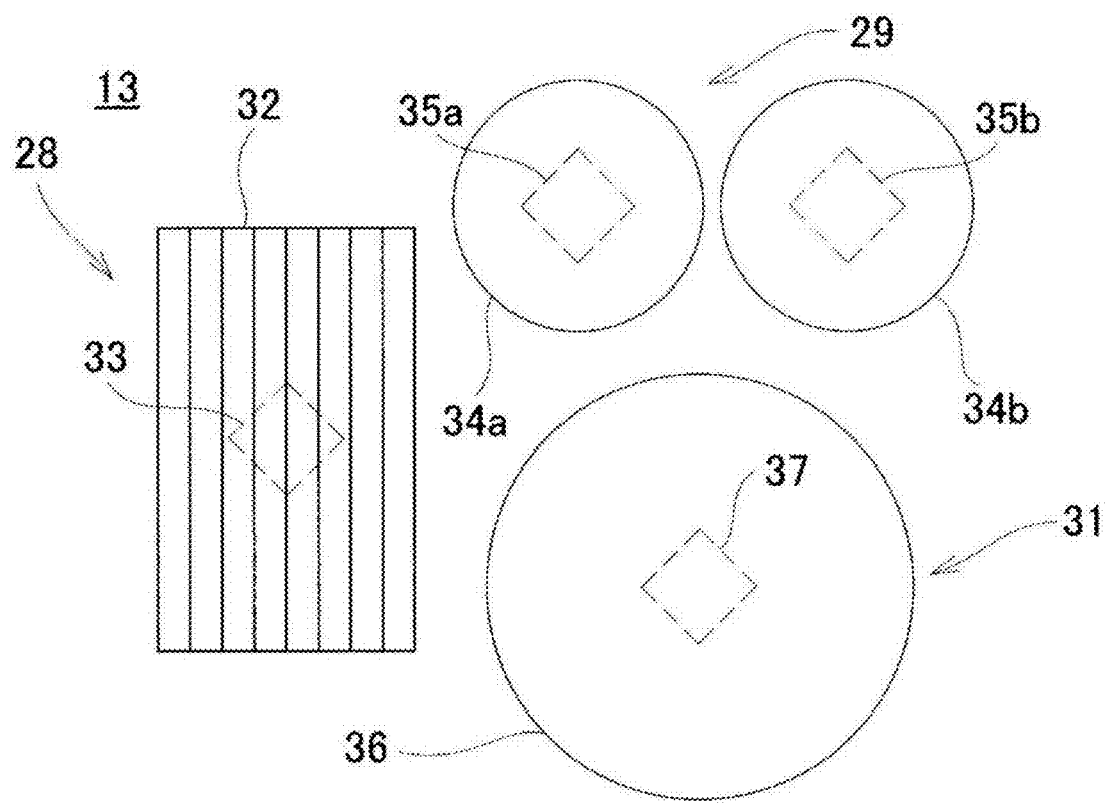
FIG. 4B is a schematic front view of the light receiving section of the measurement device.

The light receiving section 13 includes a first light receiving unit 28, a second light receiving unit 29, and a third light receiving unit 31 (see FIGS. 4A and 4B). The first light receiving unit 28 includes a first light receiving lens 32 and a first light receiving element 33, for example, a photodiode (PD). The second light receiving unit 29 includes two second light receiving lenses 34*a*, 34*b* and two second light receiving elements 35*a*, 35*b*, for example, photodiodes (PD). The third light receiving unit 31 includes a third light receiving lens 36 and a third light receiving element 37, for example, a photodiode (PD).

The first light receiving unit 28 is used mainly in measurement at a short distance by the measurement device 6. Since the measuring light 9 has a wider field angle from 40° to 70° in measurement at a short distance, the first light receiving lens 32 is composed of a cylindrical Fresnel lens in which a plurality of cylindrical lenses having such a shape, for example, a convex surface, as to receive a sufficient amount of reflected measuring light are arranged in a row with the generatrix directions thereof coinciding with the major axis direction of the measuring light 9. The cylindrical Fresnel lens enables reduction in size of the first light receiving lens 32. Note that the first light receiving lens 32 may be composed of a rotationally asymmetric anamorphic optical element.

The first light receiving element 33 has a rectangular shape such as a square or a substantially square shape. The measuring light 9 has an ellipse or an oval shape longer in the major axis direction. Thus, to efficiently receive the reflected measuring light, the first light receiving element 33 is arranged with a diagonal line of the first light receiving element 33 coinciding or substantially coinciding with the major axis of the reflected measuring light.

The second light receiving unit 29 is used mainly in measurement at a medium distance by the measurement device 6, and includes a plurality of pairs of the second light receiving lenses and the light receiving elements corresponding to the second light receiving lenses to receive a sufficient amount of light. The present embodiment includes two pairs of the light receiving lenses and the light receiving elements. Each of the second light receiving lenses 34*a*, 34*b* is composed of a circular lens having a large numerical aperture (for example, NA 0.5 or greater), such as an aspherical lens. Similar to the first light receiving element 33, the second light receiving elements 35*a*, 35*b* are arranged with diagonal lines thereof coinciding or substantially coinciding with the major axis of the reflected measuring light. Note that, in a case where a sufficient amount of light can be received with a single lens, only one of the second light receiving lenses 34*a*, 34*b* and only one of the second light receiving elements 35*a*, 35*b* may be arranged. The second light receiving lenses 34*a*, 34*b* may be composed of rotationally asymmetric anamorphic optical elements.

The third light receiving unit 31 is used mainly in measurement by a long distance at the measurement device 6. The third light receiving lens 36 is composed of a circular lens having a large numerical aperture, such as an aspherical lens, and having a larger diameter and a longer focal length than that of the second light receiving lenses 34*a*, 34*b*. Similar to the first light receiving element 33 and the second light receiving elements 35*a*, 35*b*, the third light receiving element 37 is arranged with a diagonal line thereof coinciding or substantially coinciding with the major axis of the reflected measuring light. Note that the third light receiving lens 36 may be composed of a rotationally asymmetric anamorphic optical element.

The controlling section 10 controls operations of the measurement device 6, such as light emitting control of the first light emitting element 14 and the second light emitting element 15, movement of the second cylindrical lens 26 with the motor (not illustrated), selection of a light receiving element sending a light receiving signal to be used, computation of a reflectance at each of the wavelengths based on the light receiving signal, measurement of the amount of chlorophyll contained in leaves of the crops based on the reflectance, and communication with the remote operation device 4. Note that the amount of chlorophyll contained in leaves of the crops may be measured by the remote operation device 4.

Measurement of the growth state of the crops by the measurement device 6 will be described next.

The illuminating angle of the measuring light 9 is adjusted on the basis of the distance to the crops being measurement target objects (distance to the agricultural field being a measurement target object surface), that is, the altitude of the UAV 2. The controlling section 10 acquires the flight altitude of the UAV 2 on the basis of a flight plan received from the remote operation device 4. The controlling section 10 adjusts the position of the second cylindrical lens 26 on the basis of the flight altitude and determines the illuminating angle of the measuring light 9 corresponding to the altitude of the UAV 2.

Figure 3B:
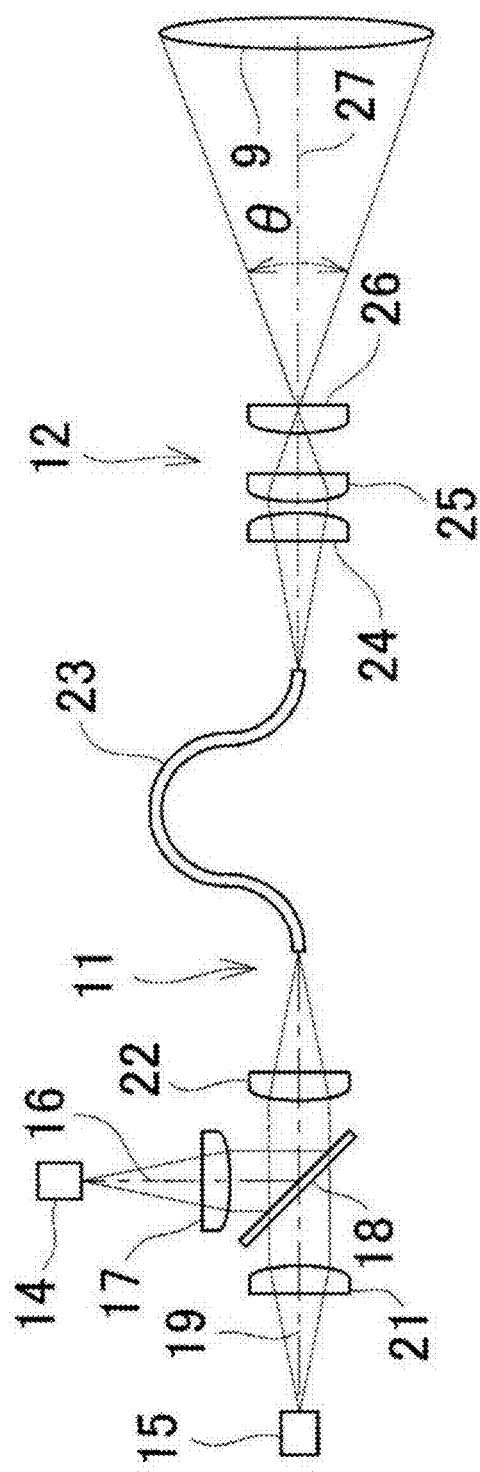

In a case where the distance to the crops is short (the altitude is low), for example, the measuring light 9 is determined to have a large illuminating angle, for example, 60°, as illustrated in FIG. 3A. In a case where the distance to the crops is long (the altitude is high), the measuring light 9 is determined to have a small illuminating angle, for example, 20°, as illustrated in FIG. 3C. In a case where the distance to the crops is medium (the altitude is medium), the measuring light 9 is determined to have a medium illuminating angle, for example, 40°, as illustrated in FIG. 3B.

Figure 5A:
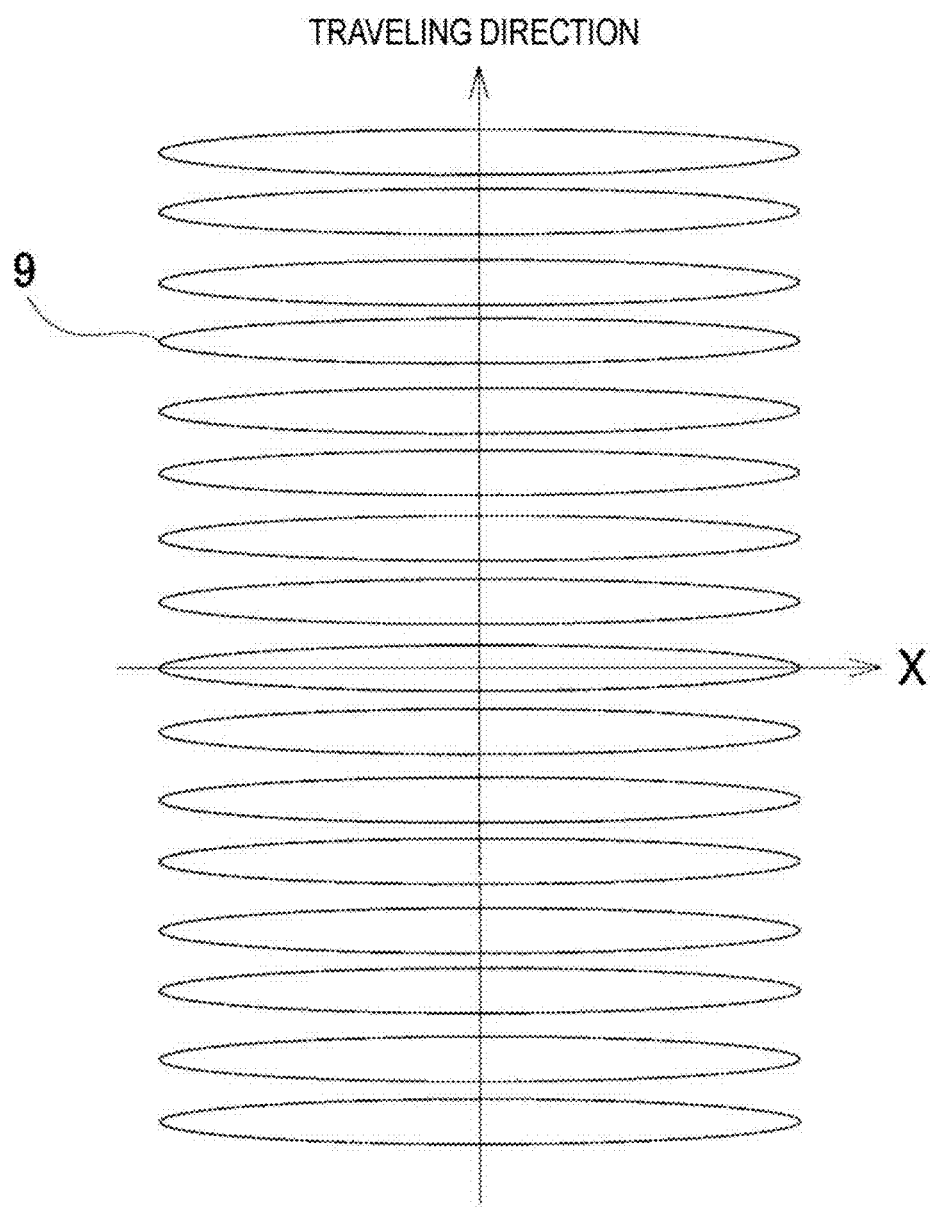
FIG. 5A is an explanatory diagram illustrating the traveling direction of a UAV and the state of illuminating a measurement target object surface with measuring light.
Figure 5B:
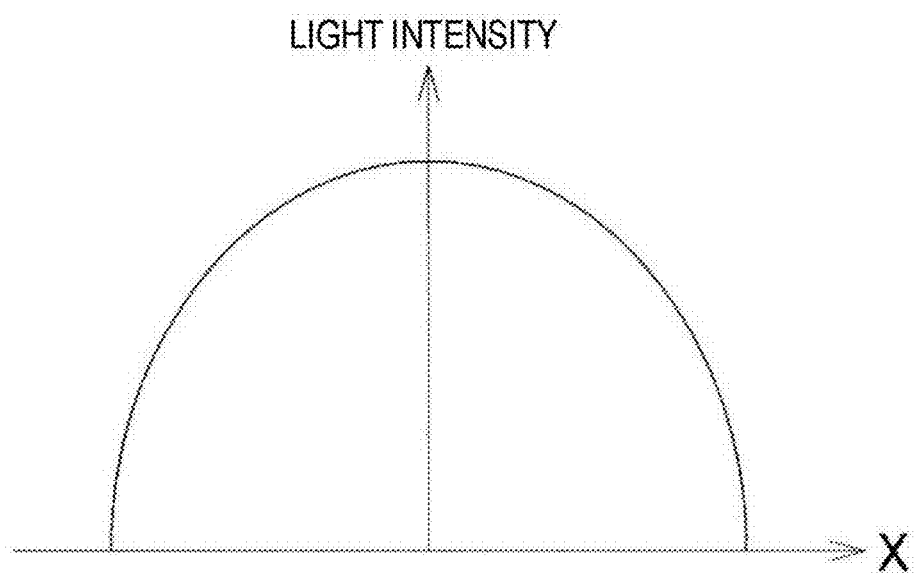
FIG. 5B is an explanatory diagram illustrating light intensity distribution of the measuring light.

After the illuminating angle of the measuring light 9 is determined, the UAV 2 flies in a predetermined measurement range on the basis of the flight plan. FIG. 5A illustrates a relationship between the traveling direction of the UAV 2 and the state of illuminating the measurement target object surface with the measuring light 9. FIG. 5B illustrates light intensity distribution of the measuring light 9 in the major axis direction (X direction).

As illustrated in FIG. 5A, the crops in the measurement range is illuminated with the ellipse or oval measuring light 9 having a major axis orthogonal to the traveling direction. As the UAV 2 travels, the crops are sequentially illuminated with the measuring light 9. Light emitting intervals of the first light emitting element 14 and the second light emitting element 15 are determined appropriately on the basis of the altitude and flight speed of the UAV 2. Note that the intervals between the illumination ranges of the measuring light 9 adjacent in the traveling direction may be greater as long as determination of the growth state is not affected. Greater intervals between the illumination ranges can increase the flight speed of the UAV 2 and can thus improve measurement efficiency.

Reflected measuring light reflected off the crops is sufficiently wide, and is thus incident on the first light receiving unit 28, the second light receiving unit 29, and the third light receiving unit 31 simultaneously. The reflected measuring light is received by the first light receiving element 33 through the first light receiving lens 32, by the second light receiving elements 35a, 35b through the second light receiving lenses 34a, 34b, and by the third light receiving element 37 through the third light receiving lens 36.

The controlling section 10 analyzes the reflected measuring light on the basis of light receiving signals from the first light receiving element 33, the second light receiving elements 35a, 35b, and the third light receiving element 37, and computes a reflectance of the reflected measuring light at each of the wavelengths. Note that the reflectance refers to, for example, a percentage of the amount of the reflected measuring light received to the amount of the measuring light 9 emitted (amount of light received/amount of light emitted×100).

In a case where the distance to the crops is short at this time, the reflected measuring light received by the first light receiving element 33 alone provides a sufficient amount of light received, so that only the light receiving signal from the first light receiving element 33 is used for the computation.

In a case where the distance to the crops is medium, the reflected measuring light received by the second light receiving elements 35a, 35b alone does not provide a sufficient amount of light received, so that the light receiving signal from the first light receiving element 33 in addition to the light receiving signals from the second light receiving elements 35a, 35b is used for the computation.

In a case where the distance to the crops is long, the reflected measuring light received by the third light receiving element 37 alone does not provide a sufficient amount of light received, so that the light receiving signals from the first light receiving element 33 and the second light receiving elements 35a, 35b in addition to the light receiving signal from the third light receiving element 37 are used for the computation.

The controlling section 10 sends the computed reflectance at each of the wavelengths to the remote operation device 4. Alternatively, the controlling section 10 computes the amount of chlorophyll contained in leaves of the crops on the basis of the computed reflectance at each of the wavelengths, and sends a result of the computation to the remote operation device 4. Note that the computation result from the controlling section 10 may be stored in a storage section, such as a memory, embedded in the measurement device 6 and retrieved after measurement in the entire measurement range is completed.

The three-dimensional position of the UAV 2 is measured by the total station 3 in real time. The remote operation device 4 correlates the timing of the measurement by the measurement device 6 with the three-dimensional position of the UAV 2 at that timing, displays the correlation on a display section (not illustrated) of the remote operation device 4, and stores the correlation in a storage section (not illustrated). The remote operation device 4 may also generate a growth map of the entire measurement range on the basis of measurement data after measurement in the entire measurement range is completed.

Thus, the growth state of the crops in a desired position in the measurement range can be known, and appropriate fertilization control of the crops can be performed.

As described above, in the first embodiment, the illuminating section 12 for illumination with the measuring light 9 is provided with the illuminating angle varying unit composed of the first cylindrical lens 25 and the second cylindrical lens 26. The first cylindrical lens 25 is fixed, and the second cylindrical lens 26 is movable in the optical axis direction, so that the distance between the first cylindrical lens 25 and the second cylindrical lens 26 is adjustable. Note that the second cylindrical lens 26 may be fixed, and the first cylindrical lens 25 may be movable.

This configuration enables the illuminating angle of the measuring light 9 to be adjusted freely depending on the distance to the crops being the measurement target objects and thus enables the single measurement device 6 to measure the growth state of the crops regardless of the distance to the crops or the area of the measurement range, resulting in reduction in measurement cost.

In the first embodiment, the first light receiving lens 32 is composed of a cylindrical Fresnel lens in which a plurality of cylindrical lenses are arranged in a row with the generatrix directions thereof coinciding with the major axis direction of the reflected measuring light. In measurement at a short distance in which the illuminating angle of the measuring light 9 is larger, this configuration can increase the amount of light received and shorten the entire length of the optical system in comparison with the case of using a rotationally symmetric lens having a large numerical aperture, resulting in reduction in size and weight of the measurement device 6.

On the other hand, in the first embodiment, the second light receiving lenses 34a, 34b and the third light receiving lens 36 are composed of rotationally symmetric lenses having a large numerical aperture. In measurement at a medium distance and a long distance in which the illuminating angle of the measuring light 9 is smaller, this configuration can increase the amount of light received and shorten the entire length of the optical system in comparison with the case of using cylindrical Fresnel lenses.

While the amount of the reflected measuring light received is ensured, the entire length of the optical system of the light receiving section 13 can be shortened, resulting in reduction in size of the measurement device 6.

Only the light receiving signal from the first light receiving element 33 is used in measurement at a short distance. The light receiving signals from the first light receiving element 33 in addition to the second light receiving elements 35a, 35b are used in measurement at a medium distance. The light receiving signals from the first light receiving element 33 and the second light receiving elements 35a, 35b in addition to the third light receiving element 37 are used in measurement at a long distance.

Thus, a necessary amount of light received is not required to be ensured only with the second light receiving unit 29 and the third light receiving unit 31, so that the second light receiving unit 29 and the third light receiving unit 31 are not required to be provided in plurality, resulting in reduction in size of the measurement device 6.

The measuring light 9 has an ellipse or an oval shape, and the first light receiving element 33, the second light receiving elements 35a, 35b, and the third light receiving element 37 are arranged with diagonal lines thereof coinciding or substantially coinciding with the major axis of the reflected measuring light. This configuration can increase the amount of light received without an increase in size of the light receiving elements, resulting in reduction in manufacturing cost.

In the first embodiment, before the crops are illuminated with the measuring light 9, the measuring light 9 is guided through the optical fiber 23 in the light source section 11. This configuration can uniformize the spatial distribution and angular distribution of the light intensity of the first laser beam and the second laser beam, resulting in improvement of measurement accuracy.

Note that in the first embodiment, all of the light receiving signals from the first light receiving element 33, the second light receiving elements 35a, 35b, and the third light receiving element 37 may be used in measurement at a short distance and a medium distance. In this case, the reflected measuring light is received mainly at the center of the light receiving elements, and a normal amount of light received can be compared with the amount of light received in the case of using all of the light receiving signals to roughly know a difference between the center and the periphery.

Figure 6:
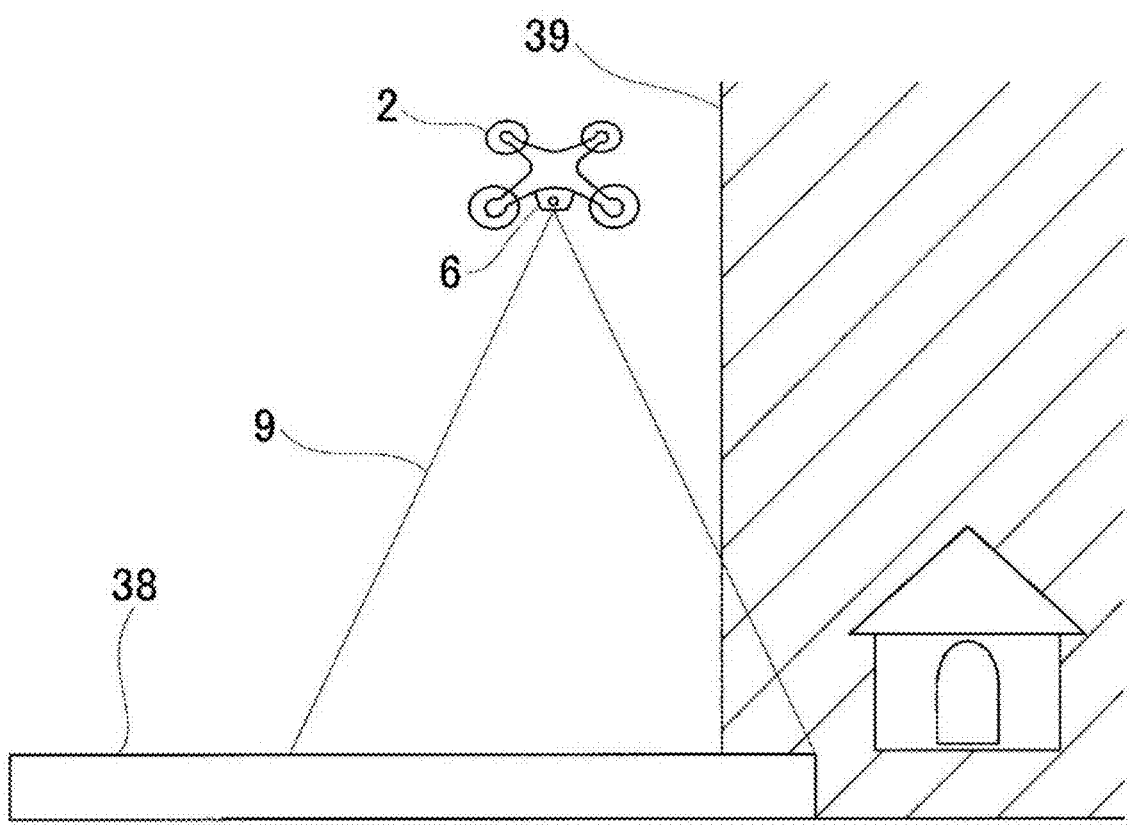
FIG. 6 is an explanatory diagram illustrating the relationship between a measurement target object surface and an illumination range when a measurement device is attached to a UAV.

The UAV 2 is provided with the measurement device 6 capable of varying a measurement distance. Thus, even in a case where the agricultural field 38 being the measurement range is partially defined as a prohibited airspace 39 for the UAV 2 as illustrated in FIG. 6, the agricultural field 38 in the prohibited airspace 39 can be illuminated with the measuring light 9 without the UAV 2 entering the prohibited airspace 39, and the entire agricultural field 38 can be measured. In the case of unstable flight of the UAV 2 due to strong wind or the like, the altitude is varied to be high, so that an accident due to unstable flight can be prevented, resulting in stable flight. Furthermore, the measurement device 6 can be used for fields 38 having various dimensions and shapes.

Note that the combined measuring light 9 is guided through the optical fiber 23 to uniformize the light intensity in the major axis direction and the minor axis direction in the first embodiment; however, in a case where the light intensity distribution of the first light emitting element 14 in the major axis direction and the minor axis direction is similar to that of the second light emitting element 15, the optical fiber 23 may be omitted as illustrated in FIG. 7. In this case, there is no need of the condenser lens 22 for condensing the measuring light 9 onto the incident end of the optical fiber 23 and the third collimator lens 24 for converting the measuring light 9 emitted from the emitting end of the optical fiber 23 into a parallel beam, so that the device configuration can be simplified, resulting in reduction in manufacturing cost.

Figure 8A:
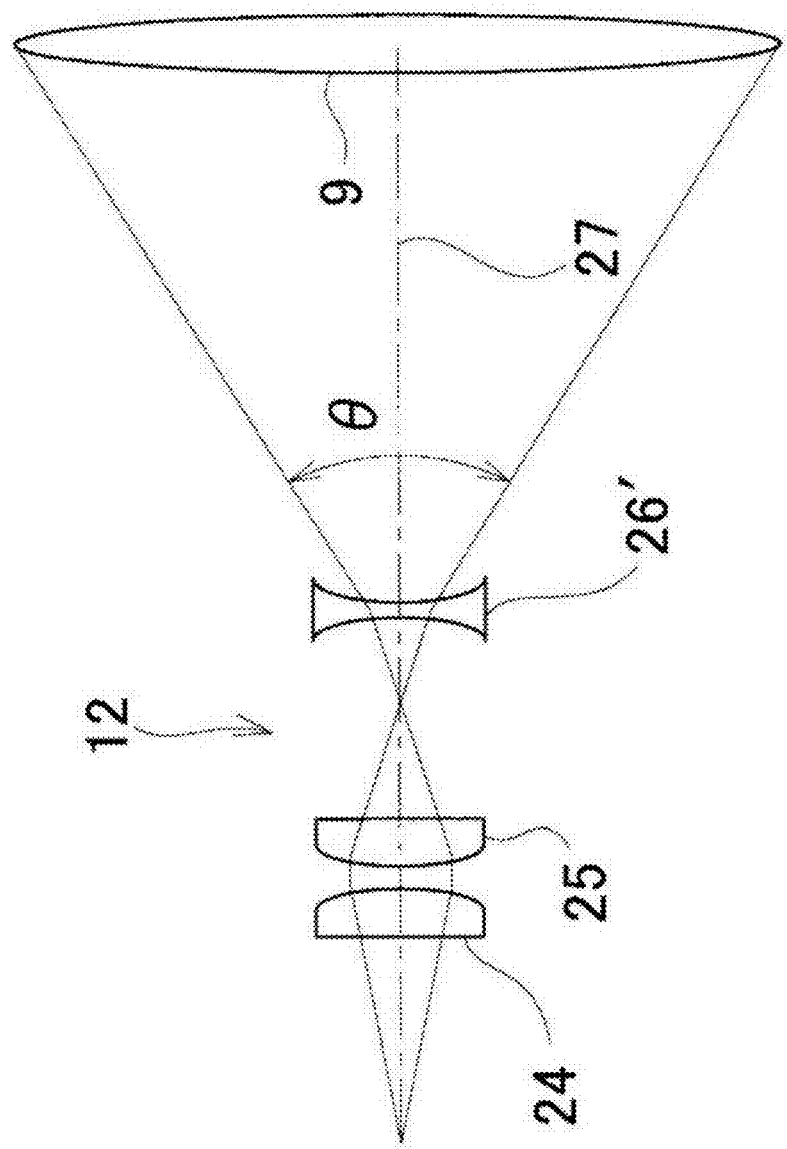
FIGS. 8A and 8B are schematic configuration diagrams of a modification of a measurement device according to the first embodiment of the invention.
Figure 8B:
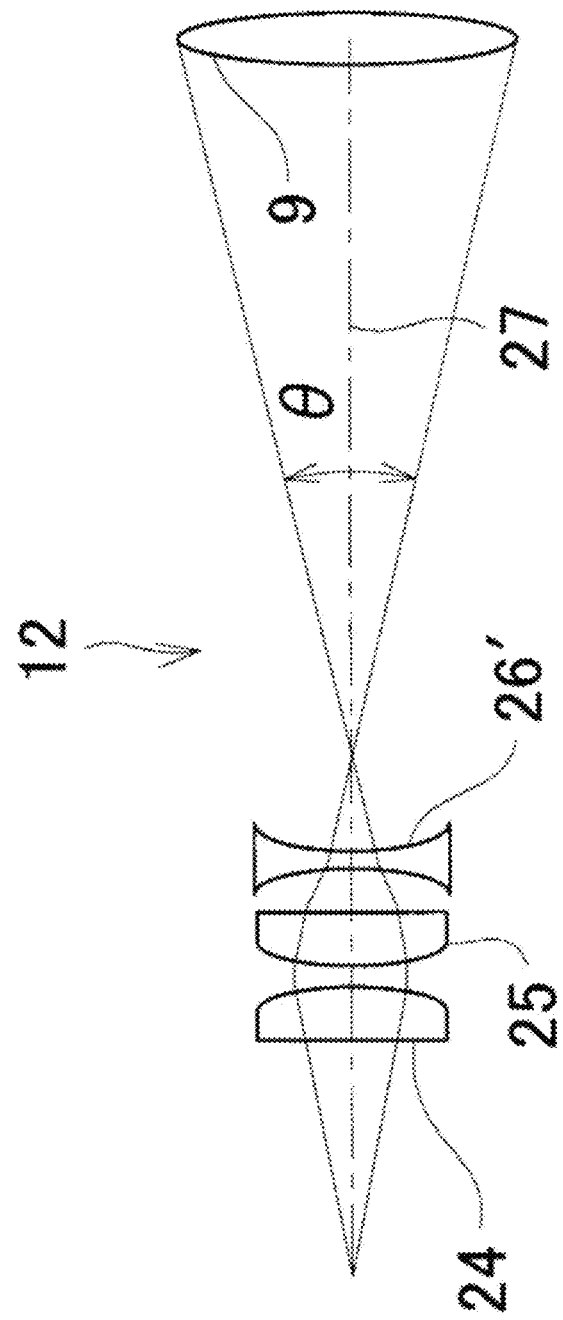

The second cylindrical lens 26 configured to move on the illumination optical axis 27 is composed of a cylindrical lens having a convex surface in the first embodiment, but a second cylindrical lens 26' having concave surfaces as illustrated in FIGS. 8A and 8B may be employed. In this case, the illuminating angle increases as the distance between the first cylindrical lens 25 and the second cylindrical lens 26' is longer and decreases as the distance is shorter. In this modification, the first cylindrical lens 25 and the second cylindrical lens 26' constitute an illuminating angle varying unit.

As illustrated in FIGS. 9A and 9B, one of the two cylindrical lenses (the second cylindrical lens 26 in FIGS. 9A and 9B) may be removably inserted to be positioned on the illumination optical axis 27, and the illuminating angle of the measuring light 9 may be varied by inserting or removing the cylindrical lens.

Figure 10A:
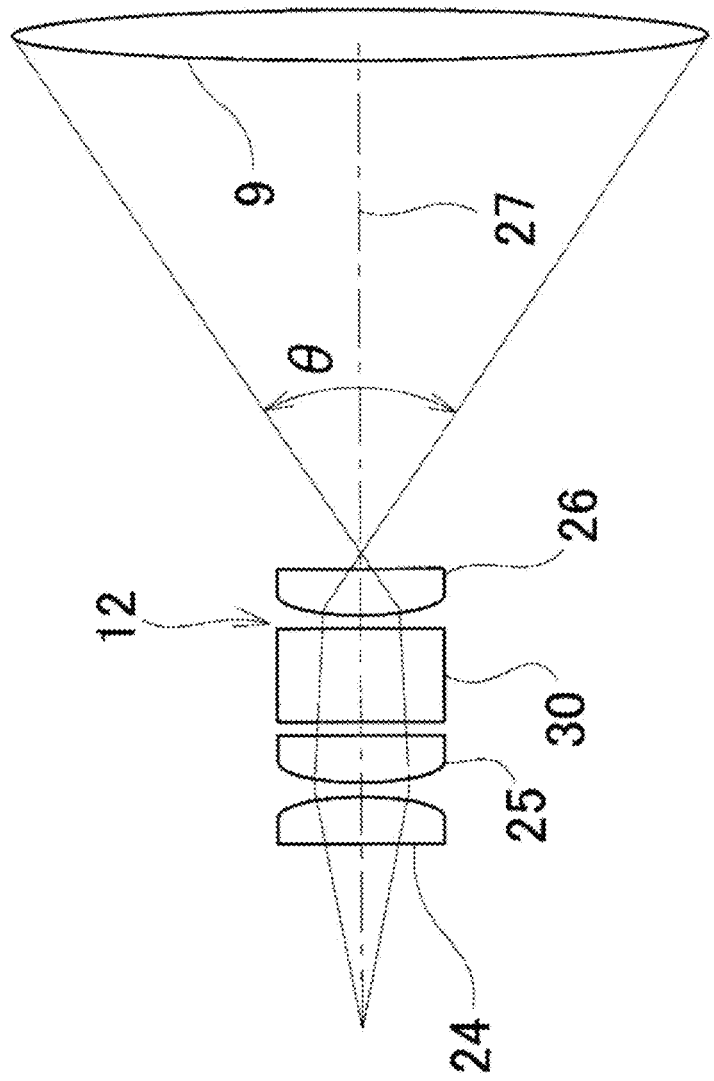
FIGS. 10A and 10B are schematic configuration diagrams of a modification of a measurement device according to the first embodiment of the invention.
Figure 10B:
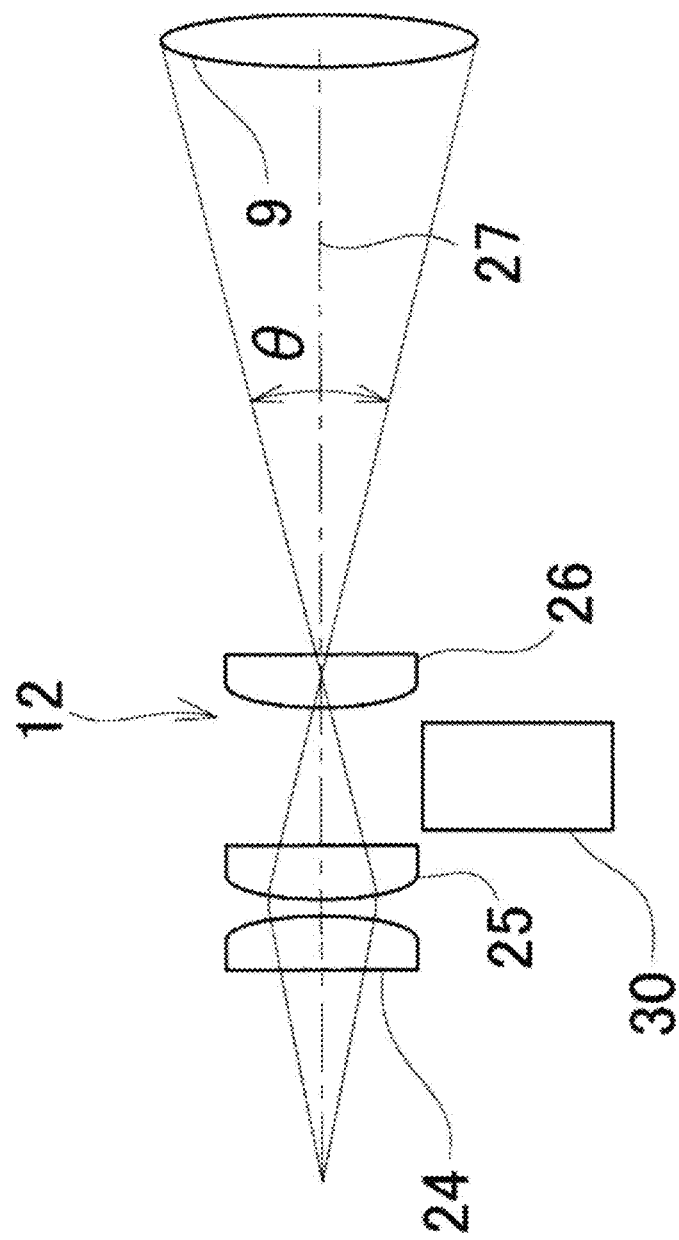

As illustrated in FIGS. 10A and 10B, a columnar optical member 30 for changing the length of the optical path of the measuring light 9 may be disposed between the first cylindrical lens 25 and the second cylindrical lens 26. By inserting the optical member 30 to position it on the illumination optical axis 27 or removing the optical member 30, the illuminating angle of the measuring light 9 can be changed.

A second embodiment of the invention will be described next with reference to FIG. 11. The second embodiment has a configuration with which the amount of the measuring light 9 increases. Note that the same reference signs are appended in FIG. 11 to equivalent parts to those of FIGS. 3A to 3C, and the description thereof is omitted. The light receiving section (not illustrated) has a configuration similar to that of the light receiving section 13 of the first embodiment.

In the second embodiment, a light source section 40 includes a first light source 41, a second light source 42, the dichroic mirror 18, the condenser lens 22, and the optical fiber 23.

The first light source 41 includes first light emitting elements 43a, 43b, first collimator lenses 44a, 44b, and a first optical deflecting member, for example, a first deflecting mirror 45. The first light emitting element 43a is composed of, for example, a laser diode (LD) and emits an S-polarized laser beam having a wavelength of 735 nm toward the first deflecting mirror 45. The first light emitting element 43b is composed of, for example, a laser diode (LD) and emits a P-polarized laser beam having a wavelength of 735 nm toward the first deflecting mirror 45. The first deflecting mirror 45 has such polarization properties as to reflect the S-polarized laser beam emitted from the first light emitting element 43a and to transmit the P-polarized laser beam emitted from the first light emitting element 43b.

Thus, after the laser beam emitted from the first light emitting element 43a is reflected off the first deflecting mirror 45 and the laser beam emitted from the first light emitting element 43b passes through the first deflecting mirror 45, the laser beams are combined.

The second light source 42 includes second light emitting elements 46a, 46b, second collimator lenses 47a, 47b, and a second optical deflecting member, for example, a second deflecting mirror 48. The second light emitting element 46a is composed of, for example, a laser diode (LD) and emits an S-polarized laser beam having a wavelength of 808 nm toward the second deflecting mirror 48. The second light emitting element 46b is composed of, for example, a laser diode (LD) and emits a P-polarized laser beam having a wavelength of 808 nm toward the second deflecting mirror 48. The second deflecting mirror 48 has such polarization properties as to reflect the S-polarized laser beam emitted from the second light emitting element 46a and to transmit the P-polarized laser beam emitted from the second light emitting element 46b.

Thus, after the laser beam emitted from the second light emitting element 46a is reflected off the second deflecting mirror 48 and the laser beam emitted from the second light emitting element 46b passes through the second deflecting mirror 48, the laser beams are combined.

The combined laser beam from the first light source 41 and the combined laser beam from the second light source 42 are further combined while passing through or being reflected off the dichroic mirror 18, and are then incident on the incident end of the optical fiber 23.

An illuminating section 12 includes the third collimator lens 24 and a fixed cylindrical lens 49 having concave surfaces. In the second embodiment, the cylindrical lens 49 constitute an illuminating unit configured to diffuse the measuring light 9.

The measuring light 9 emitted from the emitting end of the optical fiber 23 is converted into a parallel beam by the third collimator lens 24 and then diffused at a predetermined illuminating angle, for example, 60° by the cylindrical lens 49, and illuminates crops being measurement targets.

In the second embodiment, the fixed cylindrical lens 49 provides a fixed illuminating angle of the measuring light 9 regardless of the distance. However, the first light source 41 and the second light source 42 each include the two light emitting elements, and the amount of the measuring light 9 thus increases, so that a sufficient amount of light can be received even in measurement at a long distance.

The amount of light received is adjusted by appropriately selecting a light receiving element sending a light receiving signal to be used on the basis of the amounts of light received by the first light receiving element 33 (see FIG. 4A), the second light receiving elements 35a, 35b (see FIG. 4A), and the third light receiving element 37 (see FIG. 4A).

Figure 12:
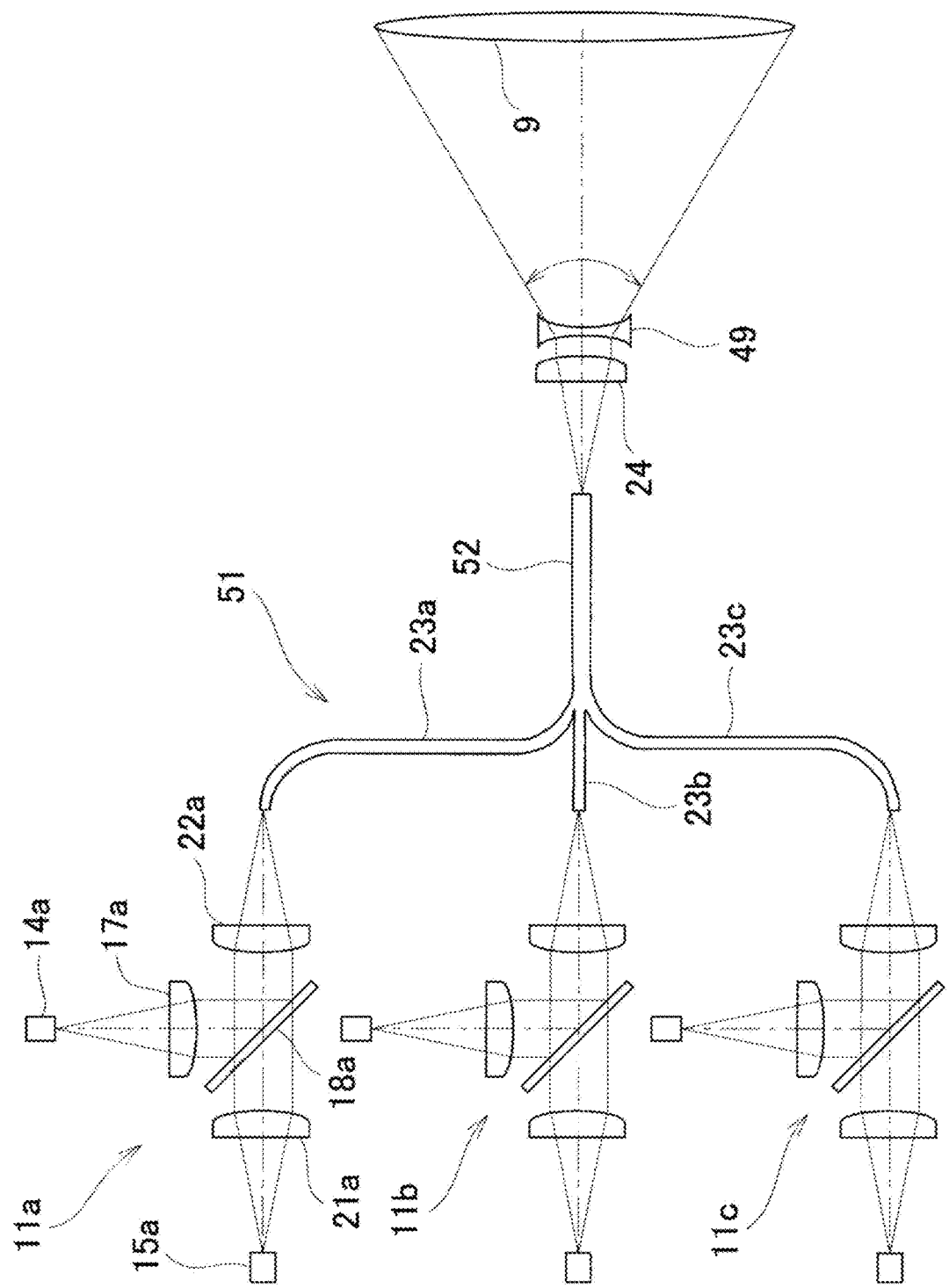
FIG. 12 is a schematic configuration diagram of a measurement device according to a third embodiment of the invention.

A third embodiment of the invention will be described next with reference to FIG. 12. The third embodiment has a configuration with which the amount of the measuring light further increases. Note that the same reference signs are appended in FIG. 12 to equivalent parts to those of FIGS. 3A to FIG. 3C and FIG. 11, and the description thereof is omitted. The light receiving section (not illustrated) has a configuration similar to that of the light receiving section 13 of the first embodiment.

A light source unit 51 of the third embodiment includes three light source sections 11a to 11c having a configuration similar to that of the light source section 11 (see FIG. 3A) of the first embodiment and a fiber combiner 52 connected with optical fibers 23a to 23c of the light source sections 11a to 11c.

The fiber combiner 52 further combines the measuring light 9 guided through the optical fibers 23a to 23c, mixes the measuring light 9 to uniformize the light intensity distribution in the major axis direction and the minor axis direction, and emits the measuring light 9 toward the illuminating section 12.

In the third embodiment, the fiber combiner 52 can combine the measuring light 9 from the plural light source sections 11, so that the amount of the measuring light 9 can increase. Thus, a sufficient amount of light can be received even in measurement at a long distance.

Similar to the second embodiment, the amount of light received is adjusted by appropriately selecting a light receiving element sending a light receiving signal to be used on the basis of the amount of light received by the first light receiving element 33 (see FIG. 4A), the second light receiving elements 35a, 35b (see FIG. 4A), and the third light receiving element 37 (see FIG. 4A). Thus, the growth state of the crops can be measured on the basis of an optimal amount of light received.

Note that the light source unit 51 includes the three light source sections 11a to 11c in the third embodiment, but may include two or four or more light source sections 11.

Figure 13:
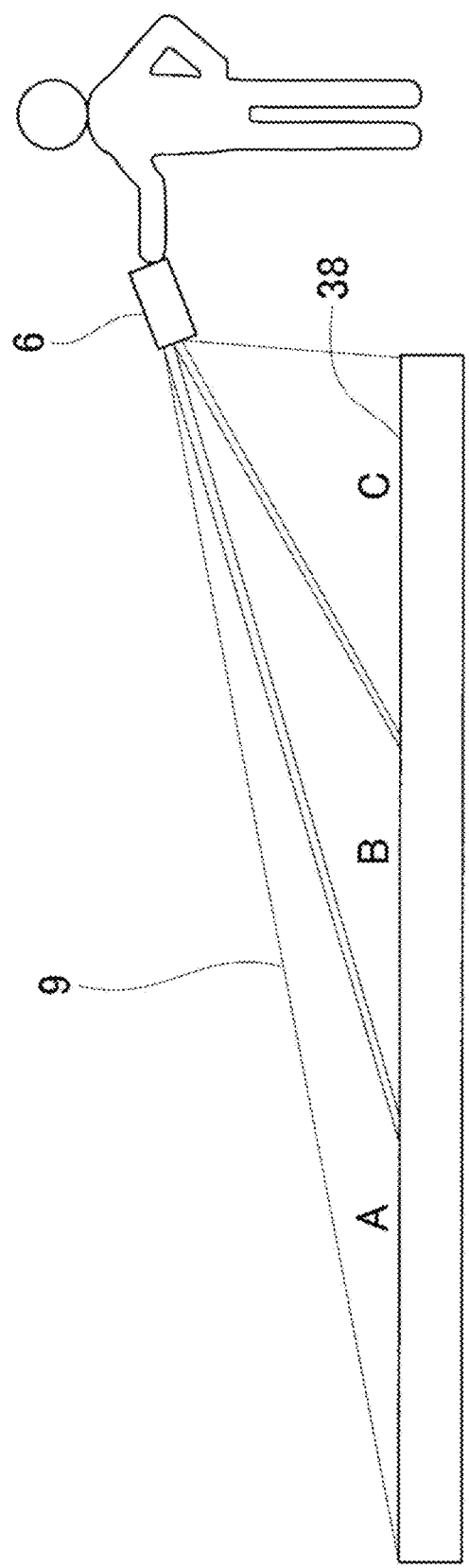
FIG. 13 is an explanatory diagram illustrating the case of using a measurement device of a hand-held type.

Note that the measurement device 6 is mounted in the UAV 2 in the first to third embodiments but may be mounted in another movable body, such as a tractor. Furthermore, as illustrated in FIG. 13, the measurement device 6 may be portable and hand-held.

In this case, an operative can freely change the illumination direction without moving and can measure crops in the agricultural field 38 while changing a measurement distance between a long distance (A region), a medium distance (B region), and a short distance (C region), resulting in improvement in workability.

Note that the measurement device 6 or the UAV 2 may include a GPS device, a compass, and an inclination sensor to measure a current position of the measurement device 6. The measurement device 6 may include a display section to display a measurement result in a position of illumination with the measuring light 9 in real time.

What is claimed is:
1. A measurement device comprising:
a light source section configured to couple a plurality of laser beams having different wavelengths and to emit measuring light;
an illuminating section configured to illuminate a measurement target with the measuring light at a predetermined illuminating angle;
a light receiving section configured to receive reflected measuring light from the measurement target; and
a controlling section configured to compute a reflectance at each of the different wavelengths, based on a light receiving result;
wherein the light source section includes:
a first light source configured to emit a laser beam having a first wavelength;
a second light source configured to emit a laser beam having a second wavelength different from a wavelength of the first light source; and
a dichroic mirror disposed in a position in which optical axes of laser beams having two wavelengths intersect, the dichroic mirror being configured to transmit one of the laser beams and reflect the other of the laser beams and to combine the laser beams having the two wavelengths,
the light receiving section includes:
a first light receiving unit configured to receive the reflected measuring light from a first distance;
a second light receiving unit configured to receive the reflected measuring light from a second distance, the second distance being greater than the first distance; and
a third light receiving unit configured to receive the reflected measuring light from a third distance, the third distance being greater than the first and second distances, and
the controlling section is configured to select which of light receiving results from the first light receiving unit, the second light receiving unit, and the third light receiving unit to use, based on a distance to the measurement target.
2. The measurement device according to claim 1, wherein the first light receiving unit includes:

a first light receiving lens including a row of cylindrical lenses having generatrix directions coinciding with a major axis direction of the reflected measuring light; and a first light receiving element configured to receive the reflected measuring light condensed through the first light receiving lens, the second light receiving unit includes:

at least one second light receiving lens having a rotationally symmetric shape and a large numerical aperture; and at least one second light receiving element configured to receive the reflected measuring light condensed through the at least one second light receiving lens, the third light receiving unit includes:

a third light receiving lens having a larger diameter and a longer focal length than a diameter and a focal length of the at least one second light receiving lens and having a rotationally symmetric shape and a large numerical aperture; and a third light receiving element configured to receive the reflected measuring light condensed through the third light receiving lens, and the controlling section is configured to use a light receiving result from the first light receiving element in measurement at the first distance, to use light receiving results from the first light receiving element and the at least one second light receiving element in measurement at the second distance, and to use light receiving results from the first light receiving element, the at least one second light receiving element, and the third light receiving element in measurement at the third distance.

3. The measurement device according to claim 2, wherein the illuminating section includes an illuminating angle varying unit disposed on an optical axis of the measuring light, and the controlling section is configured to vary an illuminating angle of the measuring light on a basis of a distance to the measurement target.

4. The measurement device according to claim 3, wherein the illuminating angle varying unit includes:

a first cylindrical lens provided in a fixed manner; and
a second cylindrical lens provided movably along the optical axis of the measuring light, and the illuminating angle varying unit allows the illuminating angle to be varied in accordance with a varied distance between the first cylindrical lens and the second cylindrical lens.

5. The measurement device according to claim 3, wherein the illuminating angle varying unit includes:

a first cylindrical lens provided in a fixed manner; and
a second cylindrical lens removably provided on the optical axis of the measuring light.

6. The measurement device according to claim 3, wherein the light source section further includes an optical fiber through which the measuring light combined by the dichroic mirror and having the two wavelengths is guided to uniformize light intensity.

7. The measurement device according to claim 2, wherein the light source section further includes an optical fiber through which the measuring light combined by the dichroic mirror and having the two wavelengths is guided to uniformize light intensity.

8. The measurement device according to claim 2, wherein the first light source includes:

two light emitting elements configured to emit laser beams having a first wavelength and arranged with polarization directions different from each other; and a first deflecting mirror configured to combine the laser beams emitted from the two light emitting elements, and the second light source includes:

two light emitting elements configured to emit laser beams having a second wavelength and arranged with polarization directions different from each other; and a second deflecting mirror configured to combine the laser beams emitted from the two light emitting elements.

9. The measurement device according to claim 2, wherein the light receiving section includes a light receiving element arranged with a diagonal line coinciding or substantially coinciding with a major axis of the reflected measuring light.

10. The measurement device according to claim 1, wherein the illuminating section includes an illuminating angle varying unit disposed on an optical axis of the measuring light, and the controlling section is configured to vary an illuminating angle of the measuring light on a basis of a distance to the measurement target.

11. The measurement device according to claim 10, wherein the illuminating angle varying unit includes:

a first cylindrical lens provided in a fixed manner; and
a second cylindrical lens provided movably along the optical axis of the measuring light, and the illuminating angle varying unit allows the illuminating angle to be varied in accordance with a varied distance between the first cylindrical lens and the second cylindrical lens.

12. The measurement device according to claim 11, wherein the light source section further includes an optical fiber through which the measuring light combined by the dichroic mirror and having the two wavelengths is guided to uniformize light intensity.

13. The measurement device according to claim 12, further comprising:

a plurality of light source sections; and
a fiber combiner configured to combine a plurality of rays of the measuring light emitted from the plurality of light source sections.

14. The measurement device according to claim 10, wherein the illuminating angle varying unit includes:

a first cylindrical lens provided in a fixed manner; and
a second cylindrical lens removably provided on the optical axis of the measuring light.

15. The measurement device according to claim 10, wherein the light source section further includes an optical fiber through which the measuring light combined by the dichroic mirror and having the two wavelengths is guided to uniformize light intensity.

16. The measurement device according to claim 1, wherein the light source section further includes an optical fiber through which the measuring light combined by the dichroic mirror and having the two wavelengths is guided to uniformize light intensity.

17. The measurement device according to claim 1, wherein the first light source includes:

two light emitting elements configured to emit laser beams having a first wavelength and arranged with polarization directions different from each other; and a first deflecting mirror configured to combine the laser beams emitted from the two light emitting elements, and the second light source includes:

two light emitting elements configured to emit laser beams having a second wavelength and arranged with polarization directions different from each other; and a second deflecting mirror configured to combine the laser beams emitted from the two light emitting elements.

18. The measurement device according to claim 1,
wherein the light receiving section includes a light receiving element arranged with a diagonal line coinciding or substantially coinciding with a major axis of the reflected measuring light.

* * * * *